United States Patent
Duff et al.

(10) Patent No.: US 9,505,682 B2
(45) Date of Patent: Nov. 29, 2016

(54) MANUFACTURE OF BUTADIENE FROM ETHYLENE

(71) Applicant: TPC Group LLC, Houston, TX (US)

(72) Inventors: Joseph G. Duff, League City, TX (US); Clifford A. Maat, Pearland, TX (US); Michael O. Nutt, Pearland, TX (US); Mark P Kaminsky, Friendswood, TX (US)

(73) Assignee: TPC GROUP LLC, Houston, TX (US)

( * ) Notice: Subject to any disclaimer, the term of this patent is extended or adjusted under 35 U.S.C. 154(b) by 193 days.

(21) Appl. No.: 14/324,428

(22) Filed: Jul. 7, 2014

(65) Prior Publication Data
US 2015/0018589 A1   Jan. 15, 2015

Related U.S. Application Data

(60) Provisional application No. 61/844,463, filed on Jul. 10, 2013.

(51) Int. Cl.
*C07C 5/48* (2006.01)
*C07C 2/30* (2006.01)

(52) U.S. Cl.
CPC . *C07C 5/48* (2013.01); *C07C 2/30* (2013.01); *C07C 2531/14* (2013.01); *C07C 2531/38* (2013.01)

(58) Field of Classification Search
CPC ............ C07C 2/08; C07C 2/10; C07C 2/00; C07C 2/02; C07C 2/04; C07C 2/06; C07C 5/00; C07C 5/32; C07C 5/321; C07C 5/322; C07C 5/324; C07C 5/373; C07C 5/48; C07C 7/00; C07C 7/04; C07C 7/11; C07C 7/12; C07C 7/09; C07C 7/08; C07C 7/20
USPC ............ 585/810, 833, 809, 807, 330, 326
See application file for complete search history.

(56) References Cited

U.S. PATENT DOCUMENTS

| | | | |
|---|---|---|---|
| 3,284,536 A | | 11/1966 | Bajars et al. |
| 3,474,155 A | * | 10/1969 | Tschopp .......... C07C 7/11 585/380 |
| 3,728,415 A | | 4/1973 | Arganbright |
| 3,911,042 A | | 10/1975 | Belov et al. |
| 3,943,185 A | * | 3/1976 | Tschopp .......... C07C 5/48 585/380 |
| 3,953,370 A | | 4/1976 | Miklas |
| 3,969,429 A | | 7/1976 | Belov et al. |

(Continued)

FOREIGN PATENT DOCUMENTS

JP      2011148720 A      8/2011

OTHER PUBLICATIONS

Welch et al., Butadiene via oxidative dehydrogenation, Hydrocarbon Processing, Nov. 1978, pp. 131-136.

(Continued)

*Primary Examiner* — Sharon Pregler
(74) *Attorney, Agent, or Firm* — Michael W. Ferrell

(57) ABSTRACT

A method of producing butadiene includes: (1) dimerizing ethylene to butene followed by (2) oxidatively dehydrogenating the butene to butadiene and (3) recovering the butadiene by (i) absorbing the product with a hydrocarbon absorber oil and (ii) stripping a crude product stream from the absorber oil. The absorber oil is selected so as to be effective to sequester ethylene dimerization-derived impurities from the system.

12 Claims, 1 Drawing Sheet

(56) References Cited

U.S. PATENT DOCUMENTS

| | | |
|---|---|---|
| 4,083,844 A | 4/1978 | Gottschlich et al. |
| 4,658,074 A | 4/1987 | Bajars et al. |
| 5,162,595 A | 11/1992 | Wu |
| 5,405,817 A * | 4/1995 | Kuo ............... B01J 31/0212 502/113 |
| 7,488,857 B2 | 2/2009 | Johann et al. |
| 7,994,378 B2 | 8/2011 | Wang et al. |
| 8,088,962 B2 | 1/2012 | Klanner et al. |
| 8,395,005 B2 | 3/2013 | Coleman et al. |
| 2010/0121123 A1 | 5/2010 | Chung et al. |
| 2011/0288308 A1 | 11/2011 | Grasset et al. |
| 2014/0088331 A1 | 3/2014 | Rolland |
| 2014/0088332 A1 * | 3/2014 | Rolland ............... C07C 5/48 585/326 |

OTHER PUBLICATIONS

International Search Report and Written Opinion mailed Oct. 24, 2014.

* cited by examiner

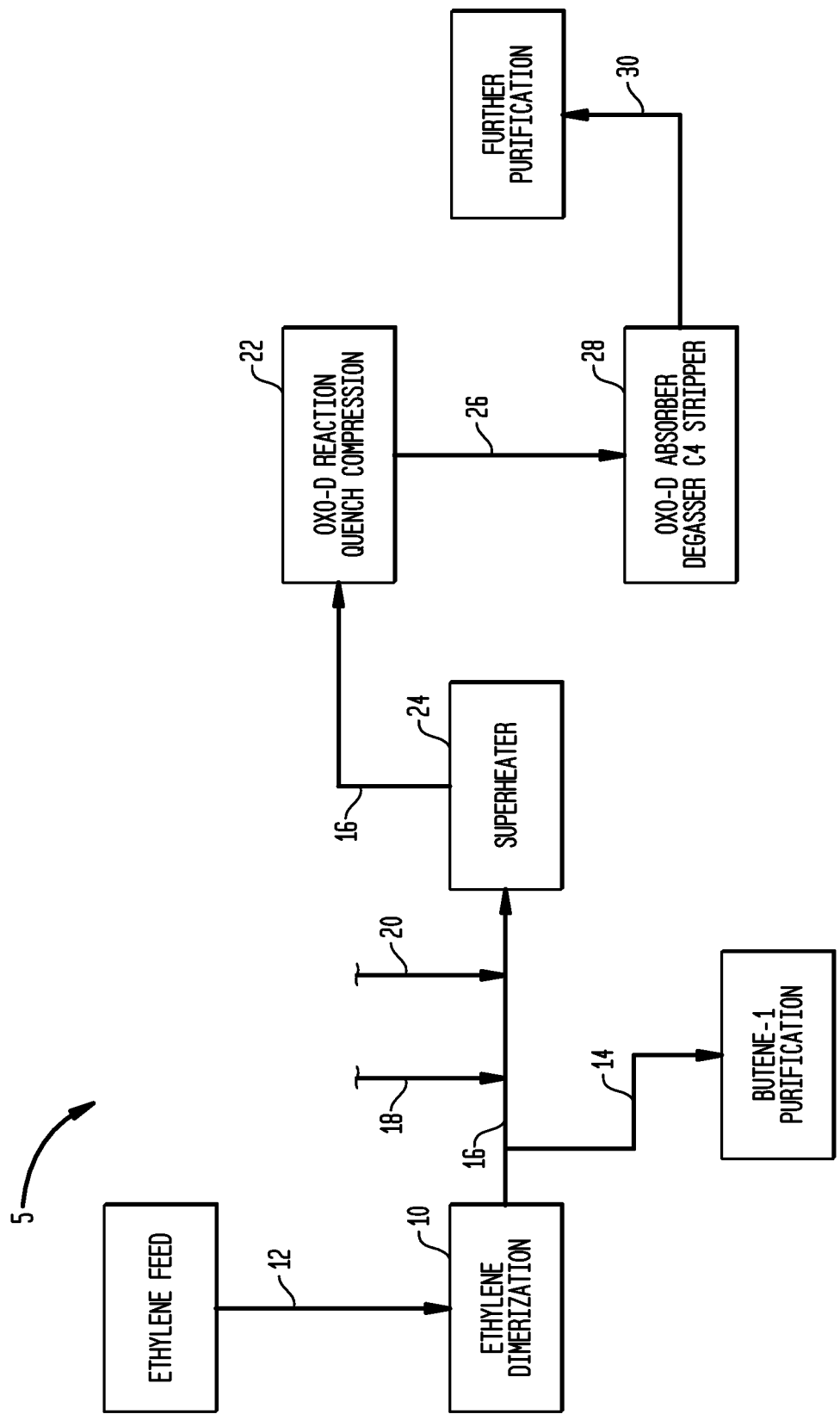

MANUFACTURE OF BUTADIENE FROM ETHYLENE

CLAIM FOR PRIORITY

This application is based upon U.S. Provisional Application No. 61/844,463, filed Jul. 10, 2013 of the same title, the priority of which is hereby claimed and the disclosure of which is incorporated herein by reference.

TECHNICAL FIELD

The present invention relates to the manufacture of butadiene by way of dimerizing ethylene to butene followed by oxidative dehydrogenation of the butene to butadiene and recovery of the butadiene produced with a hydrocarbon absorber oil.

BACKGROUND

It is known in the art to dimerize ethylene to butene and use the recovered butene for manufacturing butadiene. U.S. Pat. No. 3,728,415 to Arganbright discloses producing butenes by dimerizing ethylene with a catalyst including palladium oxide with molybdenum oxide or tungsten oxide and using the product for dehydrogenation to make butadiene.

Other references of interest include the following: U.S. Pat. Nos. 3,911,042 and 3,969,429 to Belov et al. which disclose titanium/aluminum catalyzed dimerization of ethylene and note the product is useful for making butadiene; U.S. Pat. No. 7,488,857 to Johann et al. which discloses coproduction of butadiene and butene-1 from butane; and United States Patent Application Publication No. US 2011/0288308 to Grasset et al. which discloses ethylene dimerization with titanium/aluminum catalyst.

It is proposed in Japanese Patent Publication 2011-148720 to manufacture butadiene from ethylene by way of dimerizing ethylene followed by oxidative dehydrogenation using specified catalysts to minimize impact of various impurities. The method proposed includes the following steps (I) and (II): a step (I) for producing n-butene essentially free of isobutene by dimerizing ethylene at a reaction temperature of 150 to 400° C. in the presence of a catalyst consisting of nickel, alumina, and silica having a nickel content of 0.0001 to 1 wt. %; and a step (II) for producing butadiene by performing an oxidative dehydrogenation reaction on the n-butene obtained in said step (I) with oxygen at a reaction temperature of 300 to 600° C. in the presence of a complex metal oxide comprising molybdenum and bismuth as essential ingredients.

Impurities such as isobutene associated with conventional processing are problematical as noted in the 2011-148720 Publication. Additional impurities such as trimer (C6), tetramer (C8), diolefin (butadiene, isoprene, and heavier diolefin) and acetylenic by-products of ethylene dimerization likewise present challenges to efficient operation of a butadiene manufacturing process. See also United States Patent Application Publication No. US 2014/0088332 of Rolland which relates to butadiene manufacture from ethylene using nickel and zirconium dimerization catalysts to make butenes as well as United States Patent Application Publication No. US 2014/0088331 also of Rolland which relates to butadiene manufacture from ethylene using nickel and titanium dimerization catalysts to make butenes.

SUMMARY OF INVENTION

There is provided in accordance with the present invention a method of producing butadiene by way of (1) dimerizing ethylene to butene followed by (2) oxidatively dehydrogenating the butene to butadiene and (3) recovering the butadiene by (i) absorbing the product with a hydrocarbon absorber oil and (ii) stripping a crude product stream from the absorber oil, (4) wherein the hydrocarbon absorber oil is effective to sequester ethylene dimerization-derived impurities from the system, should they be present in the reactor effluent. In accordance with the invention, undesirable ethylene dimerization-derived impurities which are not combusted in the oxidative dehydrogenation zone are absorbed into the absorber oil and may be removed from the absorber oil from time to time as necessary or simply stripped with the C4s during continuous operation of a butadiene production system and separated out in a conventional purification train.

In another embodiment, there is provided a process for co-producing butadiene and butene-1 from ethylene.

BRIEF DESCRIPTION OF DRAWING

The invention is described in detail below with reference to the drawing wherein FIG. 1 is a schematic diagram illustrating operation of an oxidative dehydrogenation process to make butene and butadiene based on ethylene as the raw material.

DETAILED DESCRIPTION

The invention is described in detail below in connection with the FIGURE for purposes of illustration, only. The invention is defined in the appended claims. Terminology used throughout the specification and claims herein are given their ordinary meanings.

Unless otherwise indicated, "butadiene" or "BD" refers to 1,3 butadiene or mixtures comprising 1,3 butadiene.

"Consisting essentially of" and like terminology refers to the recited components and excludes other ingredients which would substantially change the basic and novel characteristics of the composition. Unless otherwise indicated or readily apparent, a composition consists essentially of the recited components when the composition or article includes 90% or more by weight of the recited components. That is, the terminology excludes more than 10% of unrecited components.

"Ethylene dimerization-derived impurities" means and includes impurities such as ethylene trimers (C6), ethylene tetramers (C8), diolefins such as butadiene, isoprene, and heavier diolefins, as well as acetylenic by-products of ethylene dimerization.

Ethylene is dimerized into n-butenes suitable for use in connection with the present invention by a variety of catalytic processes. One suitable method is to utilize a homogeneous catalyst system which includes a nickel compound such as nickel phosphine oxide and an alkyl aluminum co-catalyst such as ethyl aluminum dichloride. Such processes produce predominantly 2-butenes. See, for example, U.S. Pat. No. 5,162,595 to Wu, the disclosure of which is incorporated by reference.

Alternatively, ethylene is dimerized into n-butenes suitable for use in connection with the present invention through the use of a homogeneous catalyst system which includes an organometallic titanium catalyst. In general, such processes include a titanium organometallic complex with at least one alkoxide ligand and an alkyl aluminum co-catalyst to produce predominantly 1-butene as is seen, for example, in United States Patent Application Publication No. US 2011/0288308 of Grasset et al., noted above, the disclosure of which is incorporated herein by reference. One suitable catalytic system includes titanium tetrabutoxide and triethyl aluminum. Titanium-based dimerization processes may be relatively selective, such as the Alphabutol® process and are reported to reduce fractionation costs when 1-butene of relatively high purity is required:

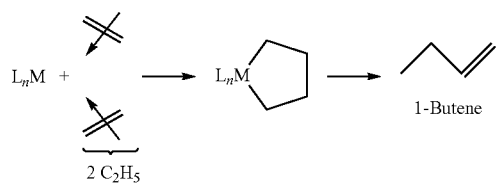

M = Metal
$L_n$ = Ligand

Substantial purification to reduce ethylene dimerization-derived impurities in the butenes produced by ethylene dimerization to less than 100 ppm is ordinarily required for most uses of the product butenes. Even at these levels, the impurities can accumulate when present in a raw material, act as catalyst poisons and be detrimental to system operation.

In accordance with the invention generally, ethylene dimerization-derived impurities present in feed to the oxidative dehydrogenation reactor are either combusted in the reactor or fed forward to the butadiene reactor effluent stream wherein they are assimilated into the absorber oil, by being absorbed by the oil. The impurities are removed from the system as necessary. Ethylene dimerization-derived impurities of 100 ppm or more in the butenes are tolerated in the feed to the oxidative dehydrogenation unit in the inventive process.

The ethylene dimerization-derived impurities produced by way of ethylene dimerization and remaining in the reactor effluent are absorbed along with C4s in the product stream using a suitable absorber oil, typically a hydrocarbon oil as described hereinafter. The butenes fed to an oxidative dehydrogenation reactor may thus contain relatively significant levels of ethylene dimerization-derived impurities as noted above. The impurities in the reactor effluent are absorbed into a suitable absorber oil along with other C4s. The ethylene dimerization-derived impurities may be removed from the oil during routine processing of the oil with absorber off-gas, removed as stripper distillate, or removed as lean oil re-run heavies. Alternatively, the impurities can be stripped from the oil with C4s and removed by later purification by conventional means. Some impurities are compatible with the absorber oil and need not be removed at all. In extreme cases, butenes may even be fed directly from a dimerization unit with reduced or even no removal of ethylene dimerization-derived impurities to an oxidative dehydrogenation unit to form butadiene if so desired; however, care should be taken to avoid very high levels of impurities since some may burn under reaction conditions and reduce yields significantly if levels are too high. The oxidative dehydrogenation production system uses a hydrocarbon absorber oil which is tolerant to ethylene dimerization-derived impurities and readily absorbs the impurities.

A typical process of the invention includes dimerizing ethylene to provide a butene rich hydrocarbonaceous feed, superheating said hydrocarbonaceous butene rich feed to a temperature of at least about 204° C. (400° F.), mixing said hydrocarbonaceous butene rich feed with superheated steam and an oxygen rich gas to form a reactor feed stream, reacting said reactor feed stream over a ferritic oxide catalyst, thereby forming a butadiene enriched product stream. Suitable ferritic oxidative dehydrogenation catalysts are also described in Miklas, METHOD OF ACTIVATING ZINC-FERRITE OXIDATIVE DEHYDROGENATION CATALYST; U.S. Pat. No. 3,953,370; Apr. 27, 1976, which relates to use of steam at a temperature of from 371-704° C. (700-1300° F.) to activate a zinc ferrite oxidative dehydrogenation catalyst for preparation of butadiene from $C_4$-$C_8$ hydrocarbons as well as Bajars et al; DEHYDROGENATION WITH MAGNESIUM FERRITE; U.S. Pat. No. 3,284,536; U.S. Pat. No. 4,083,844 to Purdy entitled CALCIUM OXIDE MODIFIED ZINC FERRITE OXIDATIVE DEHYDROGENATION CATALYSTS AND USE as well as CATALYTIC OXIDATIVE DEHYDROGENATION PROCESS; U.S. Pat. No. 4,658,074, the disclosures of which are incorporated herein by reference.

The oxidative dehydrogenation catalyst bed is preheated to a temperature which is sufficient to initiate the oxidative dehydrogenation reaction The butadiene rich reactor effluent, Details as to feed compositions and operating temperatures appear in Welch et al., *Butadiene via oxidative dehydrogenation*, Hydrocarbon Processing, November 1978, pp. 131-136, the disclosure of which is incorporated herein by reference.

The butadiene enriched product stream exiting the reactor is cooled through a quench column, in which heat is removed from the butadiene enriched product stream and steam content thereof condensed.

After passing through the quench column, the butadiene enriched product stream directed to a scrubber, and ultimately, an absorber column by absorption into a compatible absorption oil, which is adapted to preferentially absorb butadiene and other C4's as well as ethylene dimerization-derived impurities present in oxidative dehydrogenation reactor effluent.

Suitable fresh absorber oils (also sometimes referred to as lean oil) used in the absorption step can suitably be paraffinic, or a mixture of paraffins and aromatics, although particularly superior results are obtained using oils which are richer in, or possibly even entirely, vinyl cyclohexene (butadiene dimer). Suitable absorber oils are tolerant to and assimilate impurities. One preferred class of oils is a paraffinic oil having the composition shown in Table 1.

TABLE 1

Absorber Oil Composition 1

A - Normalized Weight Percent

| C-nr | Naph. | I-Par. | n-Par. | Cycl Ol. | Arom. | Total |
|---|---|---|---|---|---|---|
| 3 | | | | | | |
| 4 | | | | | | |
| 5 | | | | | | |
| 6 | 0.34 | 0.53 | 0.94 | | | 1.81 |
| 7 | | .08 | | | | 0.08 |
| 8 | .071 | 0.14 | 0.22 | | | 1.07 |
| 9 | 4.67 | .96 | 1.37 | | 0.03 | 7.02 |
| 10 | 9.80 | 4.47 | 5.70 | 0.05 | .026 | 20.28 |
| 11 | 8.76 | 21.37 | 7.12 | 0.20 | | 37.45 |
| 12+ | | 23.36 | | | | 23.36 |
| Poly | 8.94 | | | | | 8.94 |
| Total | 33.21 | 50.91 | 15.35 | 0.24 | 0.29 | 100.00 |

TABLE 1-continued

Absorber Oil Composition 1

B - Normalized Volume Percent

| C-nr | Naph. | I-Par. | n-Par. | Cycl Ol. | Arom. | Total |
|---|---|---|---|---|---|---|
| 3 | | | | | | |
| 4 | | | | | | |
| 5 | | | | | | |
| 6 | 0.35 | 0.63 | 1.10 | | | 2.08 |
| 7 | | 0.09 | | | | 0.09 |
| 8 | 0.71 | 0.15 | 0.24 | | | 1.11 |
| 9 | 4.61 | 1.02 | 1.48 | | 0.03 | 7.14 |
| 10 | 9.38 | 4.65 | 6.06 | 0.04 | 0.23 | 20.37 |
| 11 | 8.23 | 21.73 | 7.47 | 0.19 | | 37.62 |
| 12+ | | 23.75 | | | | 23.75 |
| Poly | 7.85 | | | | | 7.85 |
| Total | 31.14 | 52.02 | 16.35 | 0.23 | 0.26 | 100.00 |

C - Summary of Components

| | |
|---|---|
| Benzene | 0.00 LV % |
| Total Aromatics | 0.26 LV % |
| Total Olefins | 0.23 LV % |
| Total Saturates | 99.51 LV % |
| Total Oxygen | 0.00 Wt % | where:
C-nr = Carbon Number
Naph. = Naphthene
I-Par. = Iso-Paraffin
n-Par. = n-Paraffin
Cycl Ol. = Cyclo-olefin
Arom. = Aromatic Good results are also obtained when the fresh absorber oil is primarily Espersol 250, an aromatic naphtha product with a boiling range of 90° C. to 150° C. (200° F. to 300° F.) having the composition shown in Table 2 (Celsius Boiling Points provided in Table 2A).

TABLE 2

Absorber Oil Composition 2

| Component | Molecular Weight | N.B. Point (° F.) | Specific Gravity | Chroma. % | Assumed Wt % | Mole % | Vol. % |
|---|---|---|---|---|---|---|---|
| Benzene | 78.11 | 176.2 | 0.8845 | 6 | 5 | 6.8 | 5 |
| Cyclohexane | 84.16 | 178 | 0.783 | 3 | 2 | 2.5 | 2.3 |
| Methyl Cyclohexane | 98.18 | 213.7 | 0.774 | 1 | 1 | 1.1 | 1.1 |
| Toluene | 92.13 | 231 | 0.872 | 12 | 13 | 15 | 13.2 |
| 2,2,4-Trimethyl Pentane | 114.23 | 236.1 | 0.696 | 1 | 2 | 1.9 | 2.6 |
| Vinyl Cyclohexane | 108.18 | 262.1 | 0.8335 | 3 | 5 | 4.9 | 5.3 |
| Ethyl Cyclohexane | 112.22 | 269.2 | 0.788 | 1 | 1 | 0.9 | 1.1 |
| M&P-Xylene | 106.16 | 281 | 0.867 | 19 | 20 | 20.1 | 20.4 |
| O-Xylene | 106.16 | 291 | 0.885 | 17 | 18 | 18.1 | 18 |
| Styrene | 104.14 | 294 | 0.911 | 10 | 12 | 12.3 | 11.6 |
| Propyl Benzene | 120.19 | 318.6 | 0.862 | 1 | 2 | 1.8 | 2.1 |
| Butyl Benzene | 134.21 | 361.4 | 0.864 | 4 | 6 | 4.8 | 6.1 |
| "Heavies" (Assume 2-M Naphthalene) | 142.2 | 466 | 1.029 | 22 | 13 | 9.7 | 11.2 |

TABLE 2A

Absorber Oil Composition 2 (Celsius Boiling Points)

| Component | Molecular Weight | N.B. Point (° C.) | Specific Gravity | Chroma. % | Assumed Wt % | Mole % | Vol. % |
|---|---|---|---|---|---|---|---|
| Benzene | 78.11 | 80.11 | 0.8845 | 6 | 5 | 6.8 | 5 |
| Cyclohexane | 84.16 | 81.1 | 0.783 | 3 | 2 | 2.5 | 2.3 |
| Methyl Cyclohexane | 98.18 | 100.9 | 0.774 | 1 | 1 | 1.1 | 1.1 |
| Toluene | 92.13 | 111 | 0.872 | 12 | 13 | 15 | 13.2 |
| 2,2,4-Trimethyl Pentane | 114.23 | 113.4 | 0.696 | 1 | 2 | 1.9 | 2.6 |
| Vinyl Cyclohexane | 108.18 | 127.8 | 0.8335 | 3 | 5 | 4.9 | 5.3 |
| Ethyl Cyclohexane | 112.22 | 131.8 | 0.788 | 1 | 1 | 0.9 | 1.1 |
| M&P-Xylene | 106.16 | 138 | 0.867 | 19 | 20 | 20.1 | 20.4 |
| O-Xylene | 106.16 | 144 | 0.885 | 17 | 18 | 18.1 | 18 |
| Styrene | 104.14 | 146 | 0.911 | 10 | 12 | 12.3 | 11.6 |
| Propyl Benzene | 120.19 | 159.2 | 0.862 | 1 | 2 | 1.8 | 2.1 |
| Butyl Benzene | 134.21 | 183 | 0.864 | 4 | 6 | 4.8 | 6.1 |
| "Heavies" (Assume 2-M Naphthalene) | 142.2 | 241 | 1.029 | 22 | 13 | 9.7 | 11.2 |

After passing through the absorber column, the absorber oil having butadiene and other C4s as well as ethylene dimerization-derived impurities dissolved therein is directed to a degasser tower where carbon dioxide, residual nitrogen and hydrogen are removed, the absorber oil being passed thence to a stripper wherein butadiene product and other C4s dissolved in the absorber oil is stripped out and forwarded to further purification.

One preferred embodiment of the present invention is a co-production system 5 shown schematically in FIG. 1. Ethylene is provided to a liquid filled reactor 10 containing a titanium/aluminum homogeneous catalyst via line 12 wherein butene-1 is produced from the ethylene. The butene-1 is provided to a butene-rich product stream 14 as well as a butene-1 rich feed stream 16 with ethylene dimerization-derived impurities.

Stream 14 is purified and butene-1 (>99%) is recovered therefrom, while stream 16 is mixed with steam 18 and an oxygen rich gas 20 and provided to an oxidative dehydrogenation unit as part of a reaction/quench/compression section 22 after superheating in a superheater 24. Output 26 is enriched in butadiene and contains butene-1.

Stream 26 is fed to absorber, degasser and stripper units indicated at 28 and a crude butadiene stream 30 is recovered. Stream 30 is a majority by weight butadiene and is further purified by conventional means in order to provide butadiene of greater than 99% purity, while other C4's are recycled or otherwise recovered.

In the various embodiments of the invention, the oxidative dehydrogenation catalyst may be a ferritic catalyst, such as a ferritic oxide catalyst consisting essentially of: oxygen, a major proportion of iron; a minor proportion of zinc; and smaller amounts of manganese; phosphorus, and the residue of a nitrate free calcium precursor. The process may be operated wherein the molar ratio of oxygen to butene in the oxidative dehydrogenation reactor feed stream is from 0.4:1 to 0.8:1 and/or wherein the molar ratio of steam to butene in the oxidative dehydrogenation reactor feed stream feed stream is from 0.5:1 to 16:1.

The homogeneous reaction medium in the dimerization reactor may comprise a homogeneous catalyst comprising a nickel compound and an alkyl aluminum co-catalyst or the homogeneous catalyst may comprise a nickel phosphine oxide and ethyl aluminum dichloride in which case the butenes in the oxidative dehydrogenation reaction feed stream are predominantly 2-butenes.

The homogeneous reaction medium in the dimerization reactor may comprise a homogeneous titanium/aluminum catalyst such as a homogeneous titanium organometallic complex with at least one alkoxide ligand and an alkyl aluminum co-catalyst such as titanium tetrabutoxide and triethyl aluminum, in which cases the butene in the oxidative dehydrogenation reactor feed stream is predominantly 1-butene.

While the invention has been described in detail, modifications within the spirit and scope of the invention will be readily apparent to those of skill in the art.

In view of the foregoing discussion, relevant knowledge in the art and references, including co-pending applications, discussed above in connection with the Background and Detailed Description, the disclosures of which are all incorporated herein by reference, further description is deemed unnecessary. In addition, it should be understood that aspects of the invention and portions of various embodiments may be combined or interchanged either in whole or in part. Furthermore, those of ordinary skill in the art will appreciate that the foregoing description is by way of example only, and is not intended to limit the invention.

The invention claimed is:

1. A method of producing butadiene from an ethylene raw material feed comprising:
providing ethylene to a homogeneous reaction medium housed in a dimerization reactor;
dimerizing ethylene to butene in the homogeneous reaction medium to provide a hydrocarbonaceous butene rich feed with ethylene dimerization-derived impurities therein, wherein said ethylene dimerization-derived impurities include one or more impurities selected from ethylene trimers (C6); ethylene tetramers (C8); diolefins comprising one or more of butadiene, isoprene, and heavier diolefins; as well as acetylenic by-products of ethylene dimerization and wherein the hydrocarbonaceous butene rich feed has greater than 100 ppm of said ethylene dimerization-derived impurities;
mixing said hydrocarbonaceous butene rich feed with steam and an oxygen rich gas to form an oxidative dehydrogenation reactor feed stream and superheating said oxidative dehydrogenation reactor feed stream to a temperature of at least 204° C. (400° F.),
feeding the oxidative dehydrogenation reactor feed stream to an oxidative dehydrogenation reactor;
oxidatively dehydrogenating said reactor feed stream in the oxidative dehydrogenation a reactor over an oxidative dehydrogenation catalyst thereby forming a butadiene enriched product stream;
feeding the butadiene enriched product stream to a C4 absorber wherein C4's including butadiene and ethylene dimerization-derived impurities in the oxidative dehydrogenation reactor effluent are absorbed into a compatible absorption oil;
providing the absorption oil to a stripper in which C4 volatiles including butadiene are desorbed and stripped from said absorption oil to provide a crude product stream; and
recovering butadiene from said crude product stream.

2. The method according to claim 1, wherein the hydrocarbonaceous butene-rich feed has greater than 200 ppm of ethylene dimerization-derived impurities.

3. The method according to claim 1, wherein the hydrocarbonaceous butene-rich feed has greater than 300 ppm of ethylene dimerization-derived impurities.

4. The method according to claim 1, wherein the hydrocarbonaceous butene-rich feed has greater than 100 ppm of ethylene dimerization-derived impurities and less than 1% by weight ethylene dimerization-derived impurities.

5. The method according to claim 1, wherein the absorber oil comprises one or more compounds selected from the group consisting of toluene, xylenes, styrene and naphthalenes.

6. The method according to claim 1, wherein the absorber oil contains over 90% paraffinic compounds.

7. The method according to claim 1, wherein the absorber oil contains 90% by weight or more of compounds with atmospheric pressure boiling points of from 75° C. to 250° C.

8. The method according to claim 1, wherein the absorber contains 90% by weight or more of an aromatic naphtha product with an atmospheric pressure boiling range of from 90° C. to 150° C.

9. The method according to claim 1, wherein the absorber oil contains 90% by weight or more of vinyl cyclohexene.

10. A method of co-producing butene-1 and butadiene from an ethylene raw material feed comprising:

providing ethylene to a homogeneous reaction medium including a homogeneous titanium-aluminum catalyst housed in a dimerization reactor;

dimerizing ethylene predominantly to butene-1 in the homogeneous reaction medium to provide (i) a hydrocarbonaceous butene-1 rich feed with ethylene dimerization-derived impurities therein, wherein said ethylene dimerization-derived impurities include one or more impurities selected from ethylene trimers (C6); ethylene tetramers (C8); diolefins comprising one or more of butadiene, isoprene, and heavier diolefins; as well as acetylenic by-products of ethylene dimerization and wherein the hydrocarbonaceous butene-1 rich feed has greater than 100 ppm of said ethylene dimerization-derived impurities and (ii) a butene-1 rich product stream;

withdrawing and purifying the butene-1 rich product stream and recovering butene-1 therefrom;

mixing said hydrocarbonaceous butene-1 rich feed with steam and an oxygen rich gas to form an oxidative dehydrogenation reactor feed stream and superheating said oxidative dehydrogenation reactor feed stream to a temperature of at least 204° C. (400° F.), feeding the oxidative dehydrogenation reactor feed stream to an oxidative dehydrogenation reactor;

oxidatively dehydrogenating said reactor feed stream in the oxidative dehydrogenation reactor over an oxidative dehydrogenation catalyst thereby forming a butadiene enriched product stream;

feeding the butadiene enriched product stream to a C4 absorber wherein C4's including butadiene and ethylene dimerization-derived impurities which may be present in oxidative dehydrogenation reactor effluent, are absorbed into a compatible absorption oil;

providing the absorption oil to a stripper in which C4 volatiles including butadiene are desorbed and stripped from said absorption oil to provide a crude product stream; and recovering butadiene from said crude product stream.

11. The method according to claim 10, wherein the homogeneous titanium-aluminum catalyst comprises a titanium organometallic complex with at least one alkoxide ligand and an alkyl aluminum co-catalyst.

12. The method according to claim 10, wherein the homogeneous titanium-aluminum catalyst comprises titanium tetrabutoxide and triethyl aluminum.

* * * * *